US012083336B2

(12) United States Patent
Cruttenden et al.

(10) Patent No.: US 12,083,336 B2
(45) Date of Patent: *Sep. 10, 2024

(54) TUNABLE NEURAL ELECTRODE

(71) Applicant: Regents of the University of Minnesota, Minneapolis, MN (US)

(72) Inventors: Corey Edward Cruttenden, Minneapolis, MN (US); Rajesh Rajamani, Saint Paul, MN (US); Wei Chen, Plymouth, MN (US); Xiao-Hong Zhu, Plymouth, MN (US); Mahdi Ahmadi, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/820,115

(22) Filed: Aug. 16, 2022

(65) Prior Publication Data
US 2023/0069973 A1     Mar. 9, 2023

Related U.S. Application Data

(63) Continuation of application No. 16/039,071, filed on Jul. 18, 2018, now Pat. No. 11,439,810.
(Continued)

(51) Int. Cl.
*A61N 1/05*     (2006.01)
*A61B 5/00*     (2006.01)
(Continued)

(52) U.S. Cl.
CPC .............. *A61N 1/0534* (2013.01); *A61B 5/24* (2021.01); *A61B 5/7207* (2013.01);
(Continued)

(58) Field of Classification Search
CPC .. A61N 1/086; A61N 1/0551; A61N 1/36053; A61N 1/36062; A61N 1/36067; A61N 1/36103; A61B 5/24; A61B 5/7207
See application file for complete search history.

(56) References Cited

U.S. PATENT DOCUMENTS

| 5,964,705 A | 10/1999 | Truwit et al. |
| 7,048,716 B1 | 5/2006 | Kucharczyk et al. |

(Continued)

FOREIGN PATENT DOCUMENTS

| CN | 102824689 A | 12/2012 |
| JP | 2010246678 A | 11/2010 |
| TW | 200821576 A | 5/2008 |

OTHER PUBLICATIONS

Cruttenden et al, Novel Composite Gold-Aluminum Electrode with Application to Neural Recording and Stimulation in Ultrahigh Field Magnetic Resonance Imaging Scanners, Sep. 2021, Ann Biomed Eng.; 49(9)2337-2348. (Year: 2021).*

(Continued)

*Primary Examiner* — Rex R Holmes
*Assistant Examiner* — Jennifer L Ghand
(74) *Attorney, Agent, or Firm* — Schwegman Lundberg & Woessner, P.A.

(57) ABSTRACT

A device includes a substrate, an electrode, an electrical pad, and a signal line. The signal line is coupled to the substrate and covered by an insulation layer. The signal line is coupled to the electrical pad and the electrode. At least one of the electrode and the signal line includes a diamagnetic material and paramagnetic material, wherein a ratio of the diamagnetic material and the paramagnetic material is selected based on the susceptibility properties of a physiological tissue. The term paramagnetic herein refers to magnetic susceptibility greater than that of the surrounding tissue and
(Continued)

diamagnetic refers to magnetic susceptibility lower than that of the tissue.

8 Claims, 6 Drawing Sheets

Related U.S. Application Data (60) Provisional application No. 62/533,873, filed on Jul. 18, 2017.

(51) Int. Cl.
*A61B 5/24* (2021.01)
*A61N 1/08* (2006.01)
*A61N 1/36* (2006.01)

(52) U.S. Cl.
CPC .......... *A61N 1/0551* (2013.01); *A61N 1/086* (2017.08); *A61B 5/6868* (2013.01); *A61B 5/6877* (2013.01); *A61B 2562/125* (2013.01); *A61N 1/36003* (2013.01); *A61N 1/36053* (2013.01); *A61N 1/36062* (2017.08); *A61N 1/36067* (2013.01); *A61N 1/36103* (2013.01)

(56) References Cited

U.S. PATENT DOCUMENTS

| | | | |
|---|---|---|---|
| 8,805,536 B2 | 8/2014 | Li et al. | |
| 2005/0113676 A1 | 5/2005 | Weiner et al. | |
| 2007/0106332 A1 | 5/2007 | Denker et al. | |
| 2008/0140195 A1 | 6/2008 | Su et al. | |
| 2008/0255439 A1* | 10/2008 | Tang | A61B 5/24 600/373 |
| 2009/0191087 A1 | 7/2009 | Klein et al. | |
| 2009/0243584 A1* | 10/2009 | Zhang | C25D 11/12 205/135 |
| 2010/0234929 A1 | 9/2010 | Scheuermann | |
| 2012/0133363 A1 | 5/2012 | Mareci et al. | |
| 2014/0288618 A1 | 9/2014 | Li et al. | |
| 2014/0329707 A1 | 11/2014 | Naughton et al. | |
| 2015/0099959 A1* | 4/2015 | Bonmassar | A61N 1/0531 600/377 |
| 2018/0160929 A1* | 6/2018 | Ashe | A61B 5/291 |
| 2019/0022375 A1 | 1/2019 | Cruttenden et al. | |
| 2021/0244304 A1* | 8/2021 | Park | H01B 1/124 |

OTHER PUBLICATIONS

"U.S. Appl. No. 16/039,071, Advisory Action mailed Mar. 15, 2022", 3 pgs.
"U.S. Appl. No. 16/039,071, Final Office Action mailed Dec. 7, 2021", 11 pgs.
"U.S. Appl. No. 16/039,071, Non Final Office Action mailed Mar. 3, 2021", 12 pgs.
"U.S. Appl. No. 16/039,071, Non Final Office Action mailed Jul. 23, 2020", 8 pgs.
"U.S. Appl. No. 16/039,071, Notice of Allowance mailed May 5, 2022", 10 pgs.
"U.S. Appl. No. 16/039,071, Preliminary Amendment filed Aug. 30, 2018", 3 pgs.
"U.S. Appl. No. 16/039,071, Response filed Feb. 17, 2022 to Final Office Action mailed Dec. 7, 2021", 10 pgs.
"U.S. Appl. No. 16/039,071, Response filed Apr. 7, 2022 to Advisory Action mailed Mar. 15, 2022", 8 pgs.
"U.S. Appl. No. 16/039,071, Response filed Jun. 30, 2020 to Restriction Requirement mailed May 1, 2020", 6 pgs.
"U.S. Appl. No. 16/039,071, Response filed Sep. 2, 2021 to Non Final Office Action mailed Mar. 3, 2021", 13 pgs.
"U.S. Appl. No. 16/039,071, Response filed Nov. 23, 2020 to Non Final Office Action mailed Jul. 23, 2020", 13 pgs.
"U.S. Appl. No. 16/039,071, Restriction Requirement mailed May 1, 2020", 7 pgs.
Awara, Kousuke, et al., "Thin-film electroencephalographic electrodes using multi-walled carbon nanotubes are effective for neurosurgery", BioMedical Engineering OnLine, 13:166, (2014), 8 pgs.
Chen, Wei, et al., "Retinotopic mapping of lateral geniculate nucleus in humans using functional magnetic resonance imaging", Proc. Natl. Acad. Sci. USA, 96, (Mar. 1999), 2430-2434.
Cruttenden, Corey E., et al., "Carbon nano-structured neural probes show promise for magnetic resonance imaging applications", Biomed. Phys.. Eng. Express, 4, (2018), 1-15.
Diedrichsen, Jorn, et al., "Detecting and adjusting for artifacts in fMRI time series data", NeuroImage, 27(3), (2005), 624-634.
Duffy, Ben A., et al., "MRI compatible optrodes for simultaneous LFP and optogenetic fMRI investigation of seizure-like after discharges", NeuroImage, vol. 123, (Dec. 2015), 173-184.
Guo, Yi, et al., "Biocompatibility and magnetic resonance imaging characteristics of carbon nanotube yarn neural electrodes in a rat model", BioMed. Eng. Online, 14:118, (2015), 13 pgs.
Hargreaves, Brian A., et al., "Metal-Induced Artifacts in MRI", American Journal of Roentgenology, 197(3), (Sep. 2011), 547-555.
Hsu, Wei-Jen, et al., "A Study on the Electric Property of Buckypaper by Eddy Current Testing", 2011 IEEE Nanotechnology Materials and Devices Conference, Oct. 18-21, 2011, Jeju, Korea, (2011), 137-140.
Jiang, C. Q., et al., "Artifact properties of carbon nanotube yarn electrode in magnetic resonance imaging", Journal of Neural Engineering, 10(2), (2013), 1-8.
McHenry, Erin, et al., "UMN reserchers will map, study new area of the brain through improved fMRI technology", (c) 2017 Regents of the University of Minnesota. [online]. [retrieved on Apr. 3, 2017]. Retrieved from the Internet: <URL: https://www.healthtalk.umn.edu/2016/10/14/brain-initiative-fmri-cmrr/>, (Oct. 14, 2016), 2 pgs.
Ogawa, Seiji, et al., "An approach to probe some neural systems interaction by functional MRI at neural time scale down to milliseconds", Proc. Natl. Acad. Sci., 97(20), (2000), 11026-11031.
Park, Dong-Wook, et al., "Fabrication and utility of a transparent graphene neural electrode array for electrophysiology, in vivo imaging, and optogenetics", Nature Protocols, 11, (2016), 2201-2222.
Stefanescu, M. R., et al., "A 7T fMRI study of cerebellar activation in sequential finger movement tasks", Exp. Brain Res., 228(2), (2013), 243-254.

* cited by examiner

TUNABLE NEURAL ELECTRODE

CLAIM OF PRIORITY

This application is a continuation of U.S. application Ser. No. 16/039,071, filed Jul. 18, 2018, which claims the benefit of priority of U.S. Provisional Application 62/533,873, filed Jul. 18, 2017, which are herein incorporated by reference in their entirety. U.S. application Ser. No. 16/039,071 granted on Sep. 13, 2022 as U.S. Pat. No. 11,439,810,

STATEMENT REGARDING FEDERALLY SPONSORED RESEARCH OR DEVELOPMENT

This invention was made with government support under MH111413, NS070839, MH106049, EB015894, and NS076408 awarded by National Institutes of Health and DGE-1069104 awarded by National Science Foundation. The government has certain rights in the invention.

BACKGROUND

Measurement of neural signals is a topic of interest. This can include measuring neural electrical signals with high amplification and measurement of dopamine in the brain using voltammetry. Stimulation of neural cells using invasive electrode(s) is also of strong interest. Deep brain stimulation (DBS) can be used to treat diseases such as Parkinson's disease and essential tremor, spinal cord stimulation can be used for pain management, and stimulation of the vagus nerve is being investigated for a wide variety of treatments including hypertension. Stimulation of the peripheral nervous system is also under investigation.

Additionally, magnetic resonance (MR)-compatible research tools can be useful for studying the nervous system using functional MR imaging (fMRI) and other types of neural MRI methods as well as for studying other organs of human body.

Image artifacts induced by the implanted electrodes can impair a multimodal study and outcomes. Image artifacts around implanted neural recording and/or stimulating probes can be associated with local magnetic field distortions.

Image artifacts compromise the MR-signals originating from locations nearby the implanted electrode, thus preventing the collection of co-located electrophysiology and fMRI data and introducing challenges in imaging the electrode position inside the tissue after implantation using MRI. Such artifacts are also problematic in patients implanted with stimulation electrodes such as DBS electrodes. Artifacts around the implanted DBS electrodes prevent collection of fMRI data near the electrode site, limiting the usefulness of studying the mechanisms of DBS using fMRI.

SUMMARY

This overview is intended to provide an overview of subject matter of the present patent application. It is not intended to provide an exclusive or exhaustive explanation of the invention. The detailed description is included to provide further information about the present patent application.

Example 1 is a device comprising: a substrate having a planar or curved (e.g. cylindrical) surface; at least one signal line affixed to the substrate and covered by an insulation layer, wherein each signal line is coupled to an electrical pad and/or wire and to an electrode, generally in one to one relation, and at least one electrode or signal line includes a diamagnetic material and paramagnetic material in a tuned and particular ratio selected based on a physiological tissue susceptibility property, wherein the properties of diamagnetic and paramagnetic are values relative to that of the tissue.

In Example 2, the subject matter of Example 1 optionally includes wherein the physiological tissue is a neural tissue.

In Example 3, the subject matter of Example 2 optionally includes wherein the neural tissue is in the central nervous system.

In Example 4, the subject matter of any one or more of Examples 2-3 optionally include wherein the neural tissue is in the peripheral nervous system.

In Example 5, the subject matter of any one or more of Examples 1-4 optionally include wherein the physiological tissue is a cardiac tissue.

In Example 6, the subject matter of any one or more of Examples 1-5 optionally include wherein the physiological tissue is in the musculoskeletal system.

In Example 7, the subject matter of any one or more of Examples 1-6 optionally include wherein the physiological tissue is an organ in a broad definition.

In Example 8, the subject matter of any one or more of Examples 1-7 optionally include wherein the electrode is a recording electrode.

In Example 9, the subject matter of any one or more of Examples 1-8 optionally include wherein the electrode is a stimulating electrode.

In Example 10, the subject matter of any one or more of Examples 1-9 optionally include wherein the electrode is a recording and stimulating electrode.

In Example 11, the subject matter of any one or more of Examples 1-10 optionally include wherein the tuned ratio is a volumetric ratio.

In Example 12, the subject matter of any one or more of Examples 1-11 optionally include wherein the tuned ratio is selected based on a magnetic susceptibility of the electrode or of the signal line.

In Example 13, the subject matter of any one or more of Examples 1-12 optionally include wherein the ratio is selected to substantially match the magnetic susceptibility with that of a physiological tissue.

In Example 14, the subject matter of any one or more of Examples 1-13 optionally include wherein the diamagnetic material includes gold.

In Example 15, the subject matter of any one or more of Examples 1-14 optionally include wherein the paramagnetic material includes aluminum.

In Example 16, the subject matter of any one or more of Examples 1-15 optionally include wherein the electrode or signal line includes layers of diamagnetic material and paramagnetic material.

In Example 17, the subject matter of Example 16 optionally includes wherein a layer has a thickness of between 1 and 1000 nm.

In Example 18, the subject matter of any one or more of Examples 1-17 optionally include wherein the electrode or signal line is fabricated by diffusion or co-deposition of the paramagnetic and diamagnetic materials.

In Example 19, the subject matter of any one or more of Examples 1-18 optionally include wherein the electrode or signal line includes deposited layers.

In Example 20, the subject matter of Example 19 optionally includes wherein a layer has a thickness of approximately 1-1000 nm.

In Example 21, the subject matter of any one or more of Examples 1-20 optionally include wherein the electrode or signal line is fabricated by evaporating and heating.

In Example 22, the subject matter of any one or more of Examples 1-21 optionally include wherein the electrode or signal line is fabricated by co-depositing the diamagnetic material and the paramagnetic material.

In Example 23, the subject matter of any one or more of Examples 1-22 optionally include wherein the electrode or signal line includes a network of randomly oriented conductive nanorods/nanomaterials and matched susceptibility with that of the tissue.

In Example 24, the subject matter of any one or more of Examples 1-23 optionally include wherein the electrode and the signal line are fabricated of the same material.

In Example 25, the subject matter of any one or more of Examples 1-24 optionally include wherein the electrode includes a layer of carbon nanotubes at an exposed surface.

In Example 26, the subject matter of Example 25 optionally includes wherein the layer of carbon nanotubes has a thickness of approximately 10-200 nm.

In Example 27, the subject matter of any one or more of Examples 1-26 optionally include wherein the electrode has a layer of electrically conductive polymer at an exposed surface.

In Example 28, the subject matter of Example 27 optionally includes wherein the electrically conductive polymer includes PEDOT.

In Example 29, the subject matter of any one or more of Examples 27-28 optionally include wherein the electrically conductive polymer is formed by deposition.

In Example 30, the subject matter of any one or more of Examples 1-29 optionally include wherein the electrode includes a layer of biocompatible conductive material at an exposed surface.

In Example 31, the subject matter of Example 30 optionally includes wherein the layer of biocompatible conductive material includes gold.

Example 32 is a fabrication method comprising: providing a substrate; forming at least one signal line on the substrate; forming at least one electrode, each electrode coupled to a signal line generally in a one to one relation; at least one electrode or signal line having diamagnetic material and paramagnetic material in a ratio determined by the properties of the physiological tissue, and selectively applying insulation to the signal lines, wherein the properties of diamagnetic and paramagnetic are values relative to that of the tissue.

In Example 33, the subject matter of Example 32 optionally includes wherein providing the substrate includes providing a polyimide substrate.

In Example 34, the subject matter of any one or more of Examples 32-33 optionally include wherein forming at least one electrode or signal line includes selecting a volumetric ratio between at least two materials.

In Example 35, the subject matter of Example 34 optionally includes wherein selecting the volumetric ratio includes selecting based on a magnetic susceptibility of the electrode or signal line.

In Example 36, the subject matter of any one or more of Examples 34-35 optionally include wherein selecting the volumetric ratio includes selecting to substantially match the magnetic susceptibility with that of the physiological tissue.

In Example 37, the subject matter of any one or more of Examples 32-36 optionally include wherein forming the electrode or signal line includes forming using gold.

In Example 38, the subject matter of any one or more of Examples 32-37 optionally include wherein forming the electrode or signal line includes forming using aluminum.

In Example 39, the subject matter of any one or more of Examples 32-38 optionally include wherein forming the electrode or signal line includes forming layers of diamagnetic material and paramagnetic material with respect to a physiological tissue.

In Example 40, the subject matter of Example 39 optionally includes wherein forming a layer includes forming a layer having a thickness of between 1 and 1000 nm.

In Example 41, the subject matter of any one or more of Examples 32-40 optionally include wherein forming the electrode or signal line includes fabricating by diffusion.

In Example 42, the subject matter of any one or more of Examples 32-41 optionally include wherein forming the electrode or signal line includes depositing layers.

In Example 43, the subject matter of Example 42 optionally includes wherein depositing a layer includes depositing a layer having a thickness of approximately 1-1000 nm.

In Example 44, the subject matter of any one or more of Examples 32-43 optionally include wherein forming the electrode or signal line includes evaporating and heating.

In Example 45, the subject matter of any one or more of Examples 32-44 optionally include wherein forming the electrode or signal line includes co-depositing the diamagnetic material and the paramagnetic material.

In Example 46, the subject matter of any one or more of Examples 32-45 optionally include wherein forming the electrode or signal line includes forming a network of randomly oriented conductive nanorods/nanomaterials.

In Example 47, the subject matter of any one or more of Examples 32-46 optionally include wherein forming the electrode and/or forming the signal line includes using a common fabrication technique.

In Example 48, the subject matter of any one or more of Examples 32-47 optionally include wherein forming the electrode includes forming a layer of carbon nanotubes at an exposed electrode surface.

In Example 49, the subject matter of Example 48 optionally includes wherein forming the layer of carbon nanotubes includes forming a thickness of approximately 10-200 nm.

In Example 50, the subject matter of any one or more of Examples 32-49 optionally include wherein forming the electrode includes forming a layer of electrically conductive polymer at an exposed electrode surface.

In Example 51, the subject matter of Example 50 optionally includes wherein forming the layer of electrically conductive polymer includes forming a layer of PEDOT.

In Example 52, the subject matter of any one or more of Examples 32-51 optionally include wherein forming the electrode includes forming a layer of biocompatible conductive material at an exposed electrode surface.

In Example 53, the subject matter of Example 52 optionally includes wherein forming the layer of biocompatible conductive material includes forming a gold layer.

In Example 54, the subject matter of any one or more of Examples 1-53 optionally include wherein forming a variety of MRI-compatible and biocompatible electrodes with particular susceptibility which matches the tissue susceptibility for neural recording and brain stimulation with minimal MRI susceptibility artifacts and tissue heating safety concern.

In Example 55, the subject matter of Example 54 optionally includes wherein is also applicable for other types of tissues and organs beside the brain.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The following abbreviations and symbols are used in this document:

Abbreviations

BOLD Blood-oxygen-level dependent
CNT Carbon nanotube
EPI Echo planar imaging
fMRI Functional magnetic resonance imaging
FOV Field of view
FSEMS Fast spin echo multiple slice
GEMS Gradient echo multiple slice
LFPs Local field potentials
MRI Magnetic Resonance Imaging
PDMS Polydimethylsiloxane
RMS Root-mean-square
SEM Scanning electron microscope
SNR Signal-to-noise ratio
S Signal strength (unitless)
TE Echo time
TR Repetition time

Symbols

B Magnetic induction or magnetic flux density (T)
$\Delta B_{in}$ Voxel inhomogeneity (T)
$G_f$ Frequency encoding gradient (G cm$^{-1}$)
H Magnetic field strength (A m$^{-1}$)
$T_2$ Ideal transverse magnetization relaxation time constant, decay (ms or s)
$T_{2*}$ Imperfect (real) transverse magnetization relaxation time constant, decay (ms or s)
$\gamma$ Gyromagnetic ratio (42.58 MHz T$^{-1}$ for proton)
$\mu_0$ Magnetic permeability of free space ($4\pi \times 10^{-7}$ H m$^{-1}$)
$\mu_r$ Relative permeability (unitless)
$\chi$ Magnetic volume susceptibility (unitless)
$\Phi$ Magnetic scalar potential (A)
M Magnetization (A m$^{-1}$)
A Matrix of weights for magnetic scalar potentials of interior nodes
B Matrix of weights for magnetic scalar potentials of boundary nodes
I Identity matrix
K Right side of augmented matrix [A|B] after reduction to reduced echelon form
$\vec{\Phi}$ Vector of unknown magnetic scalar potentials of interior nodes
$\vec{u}$ Vector of defined magnetic scalar potentials at boundary nodes The present subject matter concerns electrodes or electrode arrays, for example electrodes for recording of tissue signals or for performing stimulation of tissue. The electrode can be configured for recording, stimulating, or recording and stimulating. In at least one example, the present subject matter concerns MRI-compatible electrodes for recording of brain physiological signals or for performing brain stimulation in animals and humans. The electrode (or more generally, "electrode array" containing a plurality of electrodes in an array) can be tuned to have a magnetic susceptibility close to that of brain tissue. By matching the magnetic susceptibilities of the electrode array and brain tissue, the creation of magnetic imaging artifacts can be reduced or eliminated. This will enable simultaneous use of fMRI or of a variety of MRI methods and acquisition of neural physiological signals at the same spatial location in the brain. In addition to recording brain physiological signals during MRI, such MRI-compatible electrodes could be used for neural cell stimulation. Stimulating electrodes that are tuned to have magnetic susceptibility close to that of the surrounding tissue can be used in DBS, spinal cord stimulation, vagus nerve stimulation, and peripheral nerve stimulation. Normally, the presence of an electrode in tissue creates a significant artifact which affects MRI/fMRI data at and near the location of the electrode. The ability to obtain co-located and simultaneous fMRI and neural signals can help improve understanding of brain function and its treatment. The ability to obtain fMRI and structural MRI data nearby implanted stimulating electrodes can help improve understanding of the mechanisms of neural cell stimulation for treatment of various neurological diseases. It can also allow accurate imaging and localization of the implanted electrodes for significantly improving the accuracy and efficacy of implantation and treatment. While the electrode arrays are discussed with regard to neural tissue, they can similarly be used with and tuned to other tissues, for example, cardiac tissue, muscular tissue, spinal tissue, or the like.

The tuned magnetic susceptibility of the electrodes (or probes) can be achieved by using a combination of paramagnetic and diamagnetic materials relative to tissue in the appropriate volume ratios so that the resulting electrode material has a tuned magnetic susceptibility nearly equal to that of brain or other organ tissue. Herein, paramagnetic refers to magnetic susceptibility greater than that of the surrounding physiological tissue and diamagnetic refers to magnetic susceptibility lower than that of the tissue. The ratio of the diamagnetic material and the paramagnetic material can be selected based on a physiological susceptibility property of the tissue The distortion of the magnetic field caused by the difference in magnetic susceptibilities of tissue and the electrode material can also be reduced by reducing the volume of susceptibility-mismatched electrode material. Very thin layers of high surface area materials, such as carbon nanotubes (CNT) or other nanostructured materials, can increase the conductive surface area of the electrode material in contact with brain tissue. The signal lines that conduct the neural signal to external electrical interfaces and the underlying substrate can be tuned to have magnetic susceptibility equal to that of brain tissue, thus, reducing the image artifacts. While the electrode surface in immediate contact with brain tissue is very thin, has high surface area and low volume and may have less image artifacts even though its magnetic susceptibility is not perfectly matched with brain tissue. Such a combination can provide good neural signal acquisition and high conductivity in signal lines and minimal magnetic imaging artifacts.

An example of the present subject matter can be configured to function as a conductor and/or electrode-tissue interface in an MRI-compatible neural recording and/or stimulating probe. An MRI-compatible probe can enable multimodal electrophysiology including functional MRI studies with reduced image artifacts in very strong magnetic fields, together with neural electrical signal acquisition. An MRI-compatible probe can also be used to stimulate neural tissue and study the effects of stimulation across the whole brain using fMRI or other types of MRI methods. MRI-compatible probes with reduced image artifacts can enable fMRI signal acquisition nearby implanted stimulation probes for observing the mechanisms of stimulation with the aim of improving the treatment efficacy.

The image artifacts discussed in this document are particularly large in the case of electrodes with significant volume magnetic susceptibility differences from the surrounding brain tissue, for example with traditional neural recording and stimulating electrodes made of tungsten or platinum or other types of metals. Further, functional imaging sequences utilizing the blood-oxygen-level dependent (BOLD) contrast are especially artifact prone due to their echo-planar readout and T2*-weighting that makes them very sensitive to changes in magnetic susceptibility.

Another technical challenge posed by implanted electrodes is the tissue heating problem (a safety concern) during the MRI acquisition owing to the induced eddy currents near the electrodes. One example of the present subject matter includes a solution to overcome the safety concern and fabricate an electrode having reduced eddy current and tissue heating caused by radiofrequency (RF) power.

Motivation

Functional magnetic resonance imaging (fMRI) is a powerful research tool for studying the brain noninvasively and as such can be applied in both humans and animal models. fMRI can map brain activity over the whole brain at sub-mm scale with approximately 1 Hz or better temporal resolution. Therefore, fMRI is useful for studying functional connectivity at resting state and effective connectivity under a working state in the brain in both healthy and diseased states. However, the fMRI signal measures changes in cerebral blood volume, blood flow, and blood oxygenation level within brain vessels, and therefore is not a direct measure of neuronal activity. Consequently, the fMRI signal is based on the so-called blood-oxygen-level dependent (BOLD) effect. The relationship between the BOLD effect and underlying neuronal activity is not fully understood, and a better understanding is desired for improving interpretation of fMRI data and outcomes.

To study the relationship between fMRI BOLD signals and underlying neural activity, multi-modal electrophysiology-fMRI studies can be used. Such studies involve the implantation of one or more neural recording electrodes to acquire neural electrical signals in the brain. Ideally, the neural recording and fMRI are performed simultaneously and co-located. However, traditional neural recording electrodes cause artifacts in fMRI that either preclude their use in simultaneous studies completely, or cause signal cancelation/loss at the electrode location such that co-located fMRI and electrophysiological signal acquisition is prevented. These artifacts are the result of a mismatch between the magnetic susceptibility of the electrode and the surrounding tissue. According to one example, a specially created MRI-compatible neural electrode having a magnetic susceptibility tuned and matched specifically to the surrounding brain tissue can help to eliminate image artifacts and enable simultaneous, co-located study of fMRI and electrophysiological signals. Moreover, the technical advancement will allow the structural MRI or other types of MRI collection with reduced image artifacts as well as precise imaging of the implanted electrodes in brain.

Additionally, deep brain stimulation (DBS) has achieved great success over the last two decades in treatment of many brain disorders such as Parkinson's disease, dystonia, essential tremor, depression, epilepsy and obsessive-compulsive disorder. In DBS, an electrode array is implanted into a specific targeted nucleus in the deep brain and a pulsed current with a particular frequency is delivered to restore brain functions. The underlying mechanisms of DBS for treating brain diseases are not yet well understood. There is now growing interest in using MRI for monitoring and improving DBS treatment efficacy and for basic research of understanding brain function changes associated with DBS. MRI is a non-invasive neuroimaging tool, and it can provide excellent imaging contrasts for differentiating abnormal brain tissues with minimal side effects. It can be also used to map functional brain activities that will help understand the mechanism and response of DBS. However, implanted DBS electrical devices from current commercially available products (or prototypes from research sites) which use metallic materials face a daunting challenge owing severe image artifacts in MRI due to a large susceptibility difference between the electrode material and brain tissue and tissue heating (safety concern) caused by the RF power and induced eddy current near the electrode during the MRI acquisition. These hinder MRI applications in DBS patients, in particular in high/ultrahigh magnetic field MRI scanners.

By using a specially created electrode material for neural recordings that has a magnetic susceptibility tuned to match that of brain tissue, it is possible to eliminate or reduce magnetic image artifacts and to obtain spatially co-located fMRI images at neural electrodes; map the DBS electrodes, identify and optimize the electrode location, and test the brain responses to the DBS, furthering understanding of the mechanisms of DBS. Additionally, a specially tuned recording and stimulating electrode can stimulate neural tissue and record neural physiological activity during fMRI. Such technology can provide global brain fMRI and network information including co-located measurement with the electrode and localized neural electrophysiology data in response to DBS stimulation, which can be useful for studying the underlying mechanisms of DBS and improving the treatment efficacy.

Furthermore, neurons have been shown in vitro to have a high affinity for nanostructured materials such as carbon nanotubes (CNTs), reducing the likelihood of a negative immune response and the challenges associated with it. Neural cells adhere well to carbon nanotubes and grow preferentially on their surface. CNTS also have high surface area which promotes good neural signal acquisition with high signal-to-noise ratio, even with very thin CNT films which has sub-micron thickness. CNT films also have the potential to eliminate eddy currents, and thus the safety concern of tissue heating.

While carbon nanotubes may not have a magnetic susceptibility very well matched to that of brain tissue, a very thin CNT film is adequate for neural recordings. It is possible to reduce the volume of CNT used for neural recordings by having an underlying substrate that is very well matched with brain tissue and has high thickness (for improving mechanical strength) and high conductivity. The signal transmission lines that conduct the recorded neural signal to an external electrical interface can also be made from the well-tuned highly conductive materials described in this invention. Thus, by combining a small volume of nanostructured materials with large volumes of well-tuned material of appropriate magnetic susceptibility, an optimum combination of high signal-to-noise ratio, low negative immune response, low magnetic susceptibility and image artifacts and low eddy current heating can be achieved.

An example of the present subject matter can be configured as an electrode array coating and can overcome some of the challenges that currently prevent the use of MRI/fMRI and in vivo MR spectroscopy (MRS) for investigating the mechanisms underlying DBS treatment and for improvement of treatment efficacy, for studying the relationship between the BOLD signal and neural activity, and for studying the mechanisms underlying additional treatments including spinal cord stimulation and vagus nerve stimulation.

Current commercial electrodes used in DBS are made from platinum-iridium. An example of the present subject matter includes an electrode made from specially-created materials with tuned magnetic susceptibility and with additional use of nanostructured carbon nanotubes (CNTs) or other nanostructured materials of high surface area. While CNTs have been used for academic research, their benefits for MRI applications have not been recognized even in academic research papers. Some have proposed use of CNTs for DBS electrodes from the point of view of improving electrical charge collection and for better interfacing with brain tissue cells. CNTs offer additional valuable benefits for MRI imaging which are being presented for the first time in this research. An example of the present subject matter includes materials with magnetic susceptibility tuned to equal (or match) that of brain tissue. This type of tuned material will be obtained by using combinations of paramagnetic and diamagnetic materials in the correct volume ratio and geometry. The combinations of materials can be achieved by using alloys of the proposed individual material components, by using layer-by-layer depositions of the individual materials in alternate thin film layers, or by using a composite network of conductive nanorods.

1) The magnetic susceptibility of the materials described in this document is much closer to that of brain tissue than that of traditional metallic electrodes. Hence electrodes made of these materials create almost no MRI image artifacts from their presence. This becomes especially valuable at ultra-high magnetic fields where traditional metallic electrodes create image artifacts of such a magnitude as to make MRI imaging unusable at the brain regions close to that of the electrodes.

2) The locations of the electrodes including their tips can be precisely imaged and identified by high-resolution structural MRI without image distortion. This can be helpful in deep brain stimulation (DBS) for optimization of DBS electrode location and for studying the mechanism and efficacy of DBS treatment. This is also useful for studying the relationship between the BOLD signal and underlying co-located neural electrical activity.

3) CNT and other nanostructured electrode materials provide improved adherence of tissue cells to the electrode and lower the chances of inflammation or tissue scarring when used in long-term electrode implants. Furthermore, CNT and other nanostructured materials can potentially reduce eddy currents which can lead to tissue heating (a major safety concern for metal electrodes in MRI applications). Since the nanotubes/nanoflakes in the CNT electrodes are randomly distributed to disturb the eddy current flow and since CNT has lower metallic degrees than metals, these electrodes can have weaker eddy currents than metallic electrodes under the same magnetic fields. An example of the present subject matter allows exploiting the desirable properties of CNTs by combining CNT films in low volume with high volumes of other well-tuned materials with magnetic susceptibility matching that of brain tissue.

Additionally, conductive polymer coatings can be used to improve the surface roughness of such specially tuned MRI-compatible neural recording/stimulating probes. One such example includes a coating of Poly(3,4-ethylenedioxy-thiophene), also known as PEDOT. Because some polymers have a magnetic susceptibility that is close to that of tissue, a substantial thickness of conductive polymer material at the electrode recording/stimulating location can improve the electrochemical contact between the electrode and the tissue without introducing significant magnetic field distortion in high field or clinical MRI.

It is also possible to use conductive nanorods to create a rough surface for the electrochemical recording/stimulating interface. Conductive nanorods of gold and aluminum can be used to create electrodes that have specially tuned magnetic susceptibility to match brain tissue along with the roughness that improves electrochemical contact. Furthermore, the randomly oriented structure of deposited nanorods can help to reduce with eddy currents during MRI, which contribute to electrode heating and pose a safety hazard. Therefore, conductive nanorod composites replicate the advantages of CNT coatings, but can also be tuned for matching the magnetic susceptibility to brain tissue to eliminate image artifacts.

Simulation studies can be conducted on the influence of magnetic susceptibility on magnetic imaging artifacts. Such studies have used discrete numerical solutions of partial differential equations describing magnetic scalar potential distribution in continuous 2-dimensional volumes of composite materials. Simulation studies can provide information on volume thresholds and susceptibility mismatch thresholds that lead to imaging artifacts. The simulation studies can be used to micro-fabricate an electrode with well-tuned susceptibility properties.

Simulation Method

To consider the effects of both the volume magnetic susceptibility and geometry of the electrodes during MRI, a 2D magnetic field simulator can be implemented. Other have described a solver to calculate magnetic field distortions corresponding to an object of interest, where the object is discretized and the discrete magnetic susceptibility of each node is defined. The solution can utilize the magnetic scalar potential $\Phi$, which is defined per Equation 1, where H is the magnetic field strength.

$$H = -\nabla \Phi \quad \text{Equation 1}$$

One problem entails calculating the unknown magnetic scalar potentials at each node corresponding to the defined magnetic susceptibility distribution. An equation involving the magnetic susceptibility $\chi$ and magnetic scalar potential $\Phi$ is available. Specifically, for a magnetic permeability distribution $\mu_r$ (note that $\mu_r = \chi + 1$), the magnetic scalar potential $\Phi$ is constrained per Equation 2, that is the divergence of the product of the permeability and the gradient of the scalar potential is zero.

$$\nabla \cdot (\mu_r \nabla \Phi) = 0 \qquad \text{Equation 2}$$

The simulation calculates the magnetic scalar potential corresponding to a defined magnetic volume susceptibility distribution. A direct solution method is used rather than a convergent pseudo-time approach. Expanding Equation 2 in two dimensions (x and z) results in Equation 3, where z is defined to be aligned with the applied static magnetic field and x is orthogonal to z.

$$\frac{\partial \mu_r}{\partial x}\frac{\partial \Phi}{\partial x} + \mu_r \frac{\partial^2 \Phi}{\partial x^2} + \frac{\partial \mu_r}{\partial z}\frac{\partial \Phi}{\partial z} + \mu_r \frac{\partial^2 \Phi}{\partial z^2} = 0 \qquad \text{Equation 3}$$

Figure 1:
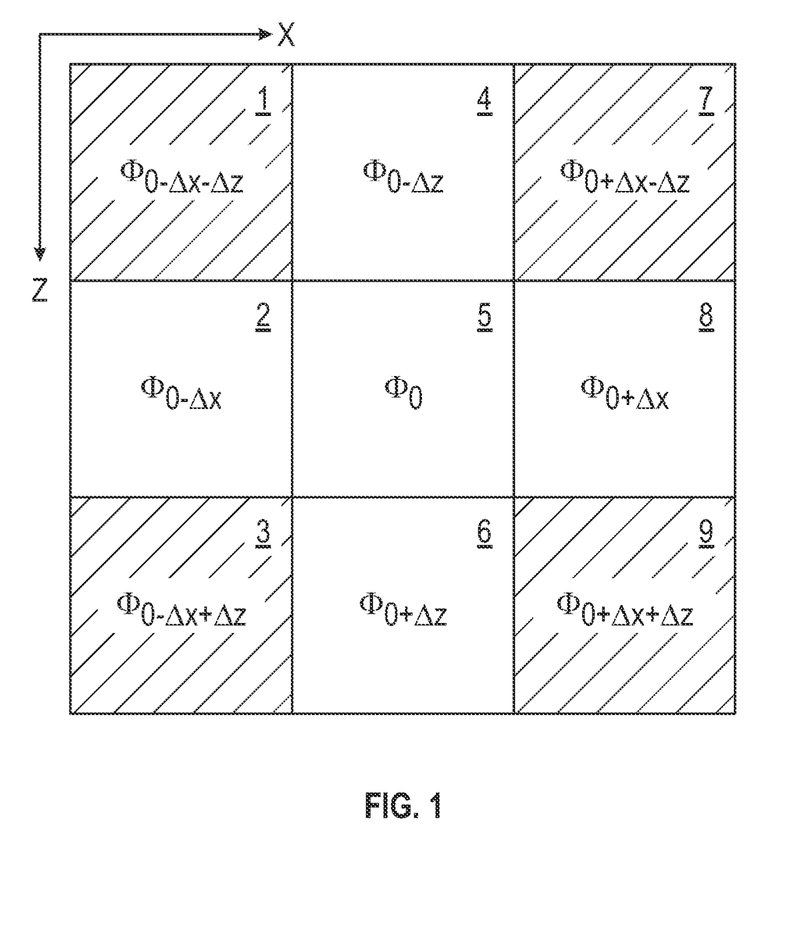
FIG. 1 illustrates discretized magnetic scalar potential for a 3×3 grid around central node 5. The shaded nodes are not used in the central difference approximations on node 5. The magnetic scalar potential can be employed to estimate the susceptibility and magnetic field distortion maps for various designs of electrodes with surrounding tissues.

Equation 3 becomes a linear system when applied on a uniform grid and approximated by finite difference methods (see FIG. 1 for a visualization of the grid). For a node with a scalar potential $\Phi_0$ (node 5 in FIG. 1), the first and second partial derivatives of $\Phi$ with respect to x and z can be approximated by the central difference method, leading to the form of Equation 4. The permeability of each node is defined to create the object of interest, so $\mu_r$ is known and the spatial partial derivatives of $\mu_r$ can be approximated by finite difference methods at each node on the grid. Therefore, $\mu_r$ and its approximate spatial derivatives are known for each node in the grid.

$$\frac{\partial \mu_r}{\partial x}\left[\frac{\Phi_{0+\Delta x} - \Phi_{0-\Delta x}}{2\Delta x}\right] + \mu_r\left[\frac{\Phi_{0+\Delta x} + \Phi_{0-\Delta x} - 2\Phi_0}{\Delta x^2}\right] +$$
$$\frac{\partial \mu_r}{\partial z}\left[\frac{\Phi_{0+\Delta z} - \Phi_{0-\Delta z}}{2\Delta z}\right] + \ldots \mu_r\left[\frac{\Phi_{0+\Delta z} + \Phi_{0-\Delta z} - 2\Phi_0}{\Delta z^2}\right] \approx 0 \qquad \text{Equation 4}$$

Equation 4 can be rearranged into the form of Equation 5, and used as a constraint on the magnetic scalar potential at each interior node, specifically a linear combination of the magnetic scalar potentials involving the central and four adjacent nodes. The partial spatial derivatives of $\mu_r$ in Equation 5 can be approximated by discrete finite difference methods, but the continuous derivative notation can be used so that the form of Equation 5 does not become unnecessarily complicated.

$$\Phi_0\left[\frac{-2\mu_r}{\Delta x^2} + \frac{-2\mu_r}{\Delta z^2}\right] +$$
$$\Phi_{0-\Delta z}\left[\frac{\mu_r}{\Delta z^2} - \frac{\partial \mu_r/\partial z}{2\Delta z}\right] + \Phi_{0+\Delta z}\left[\frac{\mu_r}{\Delta z^2} + \frac{\partial \mu_r/\partial z}{2\Delta z}\right] +$$
$$\ldots \Phi_{0-\Delta x}\left[\frac{\mu_r}{\Delta x^2} - \frac{\partial \mu_r/\partial x}{2\Delta x}\right] + \Phi_{0+\Delta x}\left[\frac{\mu_r}{\Delta x^2} + \frac{\partial \mu_r/\partial x}{2\Delta x}\right] \approx 0 \qquad \text{Equation 5}$$

The bracketed scalar weights containing magnetic permeability and grid lengths in Equation 5 can be computed for each node in the defined grid corresponding to the object of interest. Vectors $\Phi$ and u and matrices A and B are defined to satisfy the constraints for all the interior nodes in the model as described below.

$$A\vec{\Phi} + B\vec{u} = \vec{0} \qquad \text{Equation 6}$$

The vector $\Phi$ contains the unknown magnetic scalar potential at each interior node in the grid, and the vector u contains boundary conditions on the magnetic scalar potential at each boundary node. The boundary conditions can be created by placing the boundary nodes far away from the object of interest and assuming the magnetic scalar potential at the boundary is unaffected by the presence of the object. The scalar potential at the boundary can be computed through integration of Equation 1 for a particular applied field H.

Matrices A and B are systematically defined so that Equation 5 is written for each interior node of unknown magnetic scalar potential. The number of rows in A and B are equal to the number of interior nodes in the grid, that is the number of unknown magnetic scalar potentials; A is a square matrix and the number of columns in B corresponds to the number of boundary nodes minus four, as the corners of the boundaries are not used by the central difference approximations on any interior nodes. The bracketed scalar weights for each interior node are assigned to the row corresponding to that node and the appropriate column in A or B such that the weights for each node are multiplied by the appropriate scalar potential in either $\Phi$ or u. The result is a system of linear equations containing Equation 5 for every interior node in the grid. The system is represented in Equation 6 as the sum of two matrix-vector products.

To discretize an object of arbitrary curvatures in a large enough field-of-view such that the boundary magnetic scalar potentials are unaffected by the object may require several hundred nodes in each direction. In such cases, A and B are sparse matrices, e.g. for a grid of 512×512 nodes the number of columns in A and rows in A and B is 260,100, and the number of columns in B is 2,040; but the number of nonzero entries in each row of an augmented matrix [A|B] is only five, corresponding to the five magnetic scalar potentials in Equation 5. Rather than solve Equation 6 for the unknown magnetic scalar potentials in $\Phi$ by inversion of the sparse matrix A, the system can be re-written in the form of Equation 7.

$$[A \mid B]\begin{bmatrix}\vec{\Phi} \\ \vec{u}\end{bmatrix} = \vec{0} \qquad \text{Equation 7}$$

The solution is found by numerically computing the reduced row echelon form of the augmented matrix [A|B] which, by definition, has the form of the matrix in Equation 8, where I is the identity matrix the size of A.

$$[I \mid K]\begin{bmatrix}\vec{\Phi} \\ \vec{u}\end{bmatrix} = \vec{0} \qquad \text{Equation 8}$$

The unknown magnetic scalar potentials can be calculated per Equation 9.

$$\Phi = -K\vec{u} \qquad \text{Equation 9}$$

The magnetic induction or magnetic flux density B is calculated from the computed magnetic scalar potentials with finite difference approximations of Equation 10, which only applies for non-ferrous objects such that B and H are linearly related.

$$B=\mu_o\mu_r H=\mu_o\mu_r(-\nabla\Phi)$$ Equation 10

The approach described in Equations 1-10 compute the magnetic flux density, or B-field, around an object of arbitrary volume magnetic susceptibility distribution in an applied magnetic field of strength H.

The distortion of the B-field by an object can be defined as the difference between the numerically calculated B-field and the analytical background B-field in the absence of the object, normalized by the background B-field, and reported in ppm. The root-mean-square (RMS) of the distorted B-field can be used to compare the severity of field distortion across the field-of-view between simulations.

Simulation Validation and Limitations

The distortion of the static B-field by a hollow cylinder of water in air (in unit of PPM) can be mapped, and error maps between filtered numerical and analytical solutions can indicate that the numerical solution provides an accurate estimate of magnetic field distortion.

The solver has the following limitations:

1) The solver is 2D, so cross sections simulated are assumed infinitely long; the approach can be applied in 3D at the expense of computation time.

2) There is a spatial resolution vs. field-of-view (FOV) tradeoff that limits simulation of fine features on large length scales.

Simulation of Tunable Electrode Susceptibility

The following portion provides some simulation results regarding a tunable susceptibility concept. The simulation scheme is also described.

To reduce image artifacts in magnetic resonance imaging, it can be helpful to match the electrode susceptibility to that of the surrounding tissue or water. A close match in magnetic susceptibility reduces magnetic field distortions and consequently reduces image artifacts.

The static magnetic field distortions around an individual neural electrode signal line of varying material composition can be simulated. The different materials have different magnetic susceptibility values. In at least one example, the signal lines are 1.1 microns thick and 3 microns wide, which is a reasonable size for microfabricated MRI compatible neural electrode signal lines. Two orientations are considered (elongated side of signal line cross section either parallel or perpendicular to static field direction). The static field is aligned with axis z. The simulation is 2D so the signal lines are assumed infinitely long.

In some examples, only signal lines are simulated, because they are composed of metals that are not well-matched with the tissue susceptibility. Various polymer materials have a good susceptibility match to tissue that can act as substrates for the neural probes. The susceptibility map plots can have the same colormap scaling, and the field distortion maps can have the same colormap scaling for comparison purposes.

First, a copper signal line is simulated. For copper, the magnetic susceptibility difference from tissue ($\Delta\chi$) is less than 1 ppm. The copper wire cross section in the water (similar to the tissue) background cannot be distinguished with the scaling used, and the field distortions are extremely faint. Copper would be an excellent material choice in MR-compatible neural probes based on its magnetic susceptibility; however, copper is cytotoxic and will damage the neural tissue which it comes into contact. One example of the present subject matter includes an electrode of bio-compatible material having susceptibility tuning with similar or better magnetic susceptibility value compared to copper that will not damage neural tissues.

Other conductors, such as gold and aluminum, have magnetic susceptibility values significantly different than tissue and create field distortions. Aluminum is paramagnetic (positive susceptibility), while gold is diamagnetic (negative susceptibility). Therefore, a combination of these materials allows tuning the magnetic susceptibility to be equivalent to the particular value of the susceptibility of water. When mapping susceptibility and field distortion for an aluminum-based electrode or a gold-based electrode, field distortions are apparent around both electrodes, since they are not well matched in magnetic susceptibility to the surrounding tissue.

The percentage of gold in a gold-aluminum composite sufficient to achieve the effective particular susceptibility can be found by the following formula:

$$\Delta\chi_{au}(\%_{au})+\Delta\chi_{al}(1-\%_{au})=0$$

Substituting values reveals that, in theory, a gold-aluminum composite made of approximately 54% gold will have the same volume-averaged susceptibility value as water.

Two composites can be simulated. First, alternating layers of 100 nm gold and aluminum can be stacked with six layers of gold sandwiching five layers of aluminum (6/11=0.545). Such a composite structure can be fabricated using physical vapor deposition techniques (such as evaporation or sputtering), which are available in a nanofabrication facility. The results can reveal that field distortions still exist within the signal line, but the distortions outside the signal line are reduced, especially in comparison to pure gold or pure aluminum signal lines.

Additionally, a "diffused" composite of 50% gold and 50% aluminum can be simulated. Similar results can be obtained as the layer-wise stacking composite. In this example, the field distortions still exist within the signal line but distortions outside the signal line are significantly reduced compared to the case of pure aluminum or pure gold.

In viewing field distortion results for a diffused metal electrode composed of gold and aluminum, the total root-mean-square (RMS) of the magnetic field distortion across the simulated field can be shown. These results can be compared with those of copper. Copper provides a good option for reducing distortions over the whole field (both in tissue and in the signal line itself). The layering approach and diffusion approach for composite gold-aluminum materials reduces RMS distortion across the whole field but not to the same level as the copper signal line. This is because distortions still exist within the signal line for the composite materials. However, this should not result in an issue for MRI application since the electrode itself is not detected by MRI.

Consider next the distortions only within the tissue (i.e. masking out the contribution of distortions within the signal line cross-section). The composite materials approach the performance of the copper signal line. Even using a relatively coarse resolution for these simulations (e.g., 100 nm node spacing and only 128 nodes in each direction) paramagnetic and diamagnetic materials can be combined to significantly reduce the magnetic field distortions in the surrounding tissue when compared to using a pure paramagnetic or pure diamagnetic signal line. A layer-wise composite structure can be fabricated with significantly thinner layers and alloys can be fabricated with better homogeneity than those simulated. The described simulations were limited by computation time constraints. Such improvements may further reduce field distortions in the tissue and perhaps even within the signal line.

One example of the present subject matter allows tuning of the susceptibility of a composite material to match that of brain tissue, and thus, provides better performance than a copper signal line. The biocompatibility of such composites can be evaluated by comparison to cytotoxic copper and materials such as platinum or gold that are known to be biocompatible.

In Vivo Example—CNTs

A CNT electrode and a commercial linear probe array can be implanted bilaterally into the somatosensory cortex of a male Sprague-Dawley rat under isoflurane anesthesia. Anesthesia can be induced with 5% isoflurane, and then maintained between 1.5 and 3% isoflurane for the duration of the surgery and experiment. A (bilateral) craniotomy can be performed over the primary somatosensory forelimb cortex (S1FL) in each hemisphere, and electrodes can be implanted with a stereotaxic system. Neural activity can be simultaneously recorded from the probes under 1.6% isoflurane at 30 kHz using a Cerebus data acquisition system (Blackrock Microsystems, Salt Lake City, UT). An ex vivo noise floor can be recorded at the end of the experiment to compare the SNR of the probes. Noise filtering (60 Hz) can be applied during post processing in MATLAB, and signals can be low-pass filtered to isolate local field potentials (LFPs<500 Hz).

Additionally, 2-slice MR-imaging can be performed in an anesthetized rat implanted with a single CNT electrode in the left somatosensory cortex. Again, anesthesia can be induced with 5% isoflurane, and then maintained between 1.5 and 3% isoflurane for the duration of the surgery and experiment. The animal can be intubated and catheterized via the femoral artery prior to being placed in an MR-compatible cradle, and secured with bite and ear bars. A small craniotomy can be performed over the primary somatosensory forelimb cortex in the left hemisphere. A plastic anchor can be attached to the contralateral skull for electrode stabilization. The electrode can be inserted into the cortex using a stereotaxic system, and dental cement applied to secure the electrode and close the craniotomy. The animal's body temperature can be maintained at 37° C. with a heated water pad. Artificial breathing controlled by a ventilation machine can be adjusted to maintain normal blood gases. At the end of the study, a bolus of potassium chloride (KCl) can be injected into a venous line to induce a heart attack. Imaging can be performed on a 9.4T/31 cm horizontal bore magnet with a VnmrJ console (Agilent, Santa Clara, CA) and a custom RF coil. Multi-slice gradient echo (GEMS) and fast spin echo (FSEMS) sequences can be performed to acquire whole brain anatomical images in sagittal, axial, and coronal orientations with a resolution of 156.3 μm or 78.1 μm (FOV 40×40 mm, slice thickness 0.5 or 1 mm, 256×256 of 512×512 image matrix size). Functional imaging can be acquired using T2*-weighted single shot echo planar imaging sensitive to the BOLD contrast (gradient echo EPI, TR 612 ms, TE 17 ms, FOV 40×40 mm, 64×64 voxels, slice thickness 1 mm, 1-3 slices).

MRI images can be loaded into MATLAB with the AEDES toolbox. Network connectivity maps can be calculated using a seed based correlation analysis and overlaid on slice matched anatomical images with a threshold of p<0.05 and correlation coefficient |cc|>0.5.

In vivo experimentation in an anesthetized rat can reveal that one example of a CNT neural electrode can achieve higher SNR than commercial electrodes. This SNR improvement may be related to the high electrochemical surface area of the CNT electrode. Additionally, both structural and functional MR images can be obtained around an implanted CNT electrode in vivo at a field strength of 9.4 T with low artifacts as shown in FIG. 10D. The ability to obtain functional images around an implanted neural electrode with high SNR in neural signals is useful for understanding the brain, since simultaneous electrophysiology and functional hemodynamic/metabolic data could be combined.

Nanorod Composites and Eddy Current Reduction

An example of the present subject matter is configured for fabrication neural electrodes with tunable magnetic susceptibility. The magnetic susceptibility of the electrodes can be matched to that of brain tissue by using a combination of paramagnetic and diamagnetic materials in a selected proportion to obtain a combined equivalent susceptibility matched with that of the brain tissue.

The following provides an example of a particular embodiment of the present subject matter.

In one embodiment, nanorods of gold and aluminum (diamagnetic and paramagnetic respectively) can be used to form the conductive electrodes. By using randomly oriented networks of nanorods instead of a continuous layer of material, eddy currents in the electrodes caused by the changing magnetic fields in the MRI machine are reduced. Thus, an electrode of the present subject matter will both provide low MRI image artifacts and also low heating of tissue (due to low eddy currents). In at least one example, aluminum (Al) nanorods in water can be combined with gold (Au) nanorods in water. A combination of Au and Al can be used to tune magnetic susceptibility to equal or match (or substantially equal or match) that of brain tissue.

One example includes an electrode having Au and Al nanorods in a randomly oriented multi-layered network. In one example, each signal line and electrode of a neural probe can be fabricated of Al and Au nanorods mixed in the selected proportion (for example, about 46% to about 54% by volume). The nanorods can form conductive networks that are fabricated to form electrodes and signal lines. Fabrication can include etching or fabricating using lift-off techniques.

In some examples, a randomly oriented network of nanorods can be advantageous in that eddy currents induced in the loops in the network tend to cancel each other's effects. Eddy currents are expected to be very low in a conductive network compared to a continuous electrode surface. The nanorod network in the presence of a varying external magnetic field can result in a magnetic field in the opposite direction of the applied magnetic field, due to the induced current. In some examples, currents in each nanorod can cancel each other in every side of the loops. In some examples, the only remaining eddy currents in the network of nanorods are current loops induced within each nanorod. These are expected to be very low because each nanorod is very thin (e.g., tens of nanometers) and has high individual resistance due to very low cross-section area.

FURTHER EXAMPLES

Figure 2:
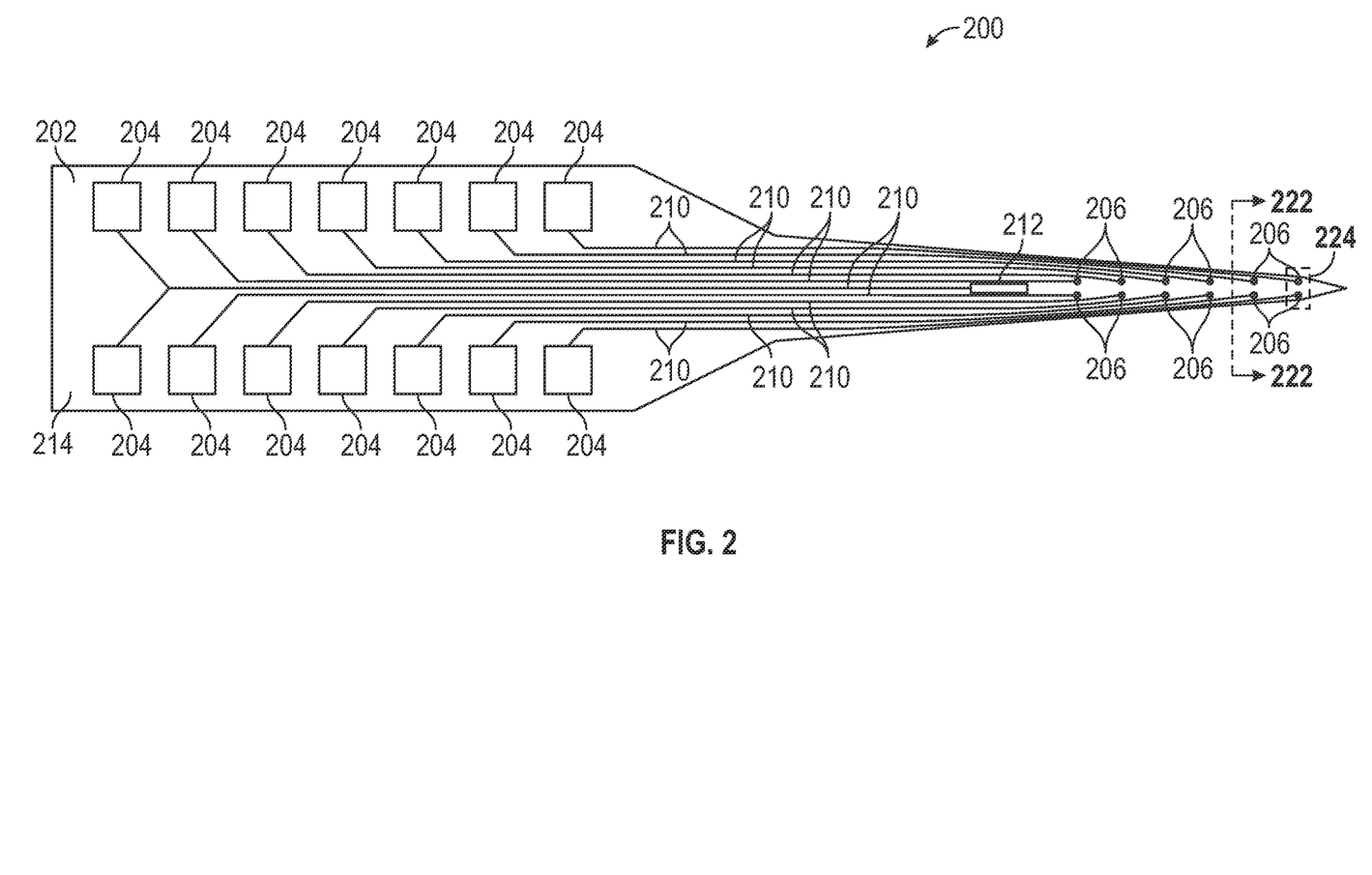
FIG. 2 illustrates an example of a neural recording or stimulating electrode, in accordance with at least one embodiment.

FIG. 2 illustrates an embodiment of an electrode array 200, for example, a neural recording electrode array. In the example shown, the electrode array 200 includes a substrate 202 having a plurality of electrical pads 204, each of which is coupled to a separate electrode 206 positioned in the penetrating substrate tip 208. Each separate electrode 206 is coupled to an electrical pad 204, in a one-to-one relation, by a signal line 210. Each signal line 210 is disposed on the substrate 202 and beneath a layer of insulation 214. In at least one example, each electrode 206 is a recording electrode. In some examples, the electrode array 200 also includes a reference electrode 212. In other examples, the electrodes 200 could be a stimulating electrode, or a recording and stimulating electrode. In some examples, one or more of the electrodes 206 can be stimulating electrodes. In at least one example, the electrical pads 204 can be coupled to another device to facilitate recording or stimulating.

The figure indicates a section taken at cut line 222-222 and a detail view at 224 near the tip of the electrode array 200. Various examples of section view 222 and detail view 224 are described in subsequent figures. Note that certain details in the figures of this document are not necessarily depicted in scale but are drawn for clarity in illustrating concepts and claims. For example, the signal lines 210 may appear nearly equal in dimension to the insulation 214 however, this is not necessarily the case.

Figure 3A:
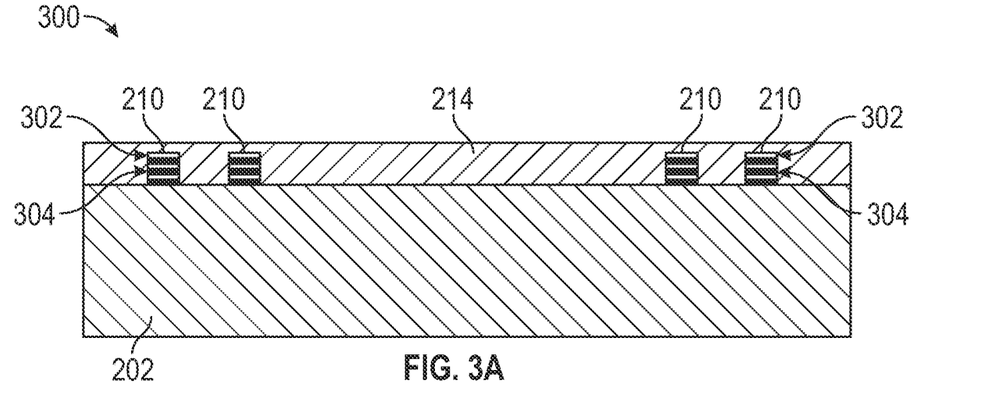
FIGS. 3A, 3B, 3C, 3D and 3E illustrate section and detail views of an electrode, in accordance with at least one embodiment.

FIG. 3A illustrates an example 300 of section view 222, and FIGS. 3B, 3C, 3D, and 3E illustrate examples of detail view 224. In the example 300 shown in FIG. 3A, the section view taken at 222-222 (with respect to FIG. 2) illustrates that the signal lines 210 are disposed on the substrate 202 and electrically isolated by the layer of insulation 214. In the illustrated example, the electrodes and signal lines 210 are fabricated of alternating layers of diamagnetic materials 302 and paramagnetic materials 304 balanced in a particular volumetric ratio such that the effective bulk magnetic susceptibility is tunable to that of neural tissue. In at least one example, the signal lines 210 can include alternating layers of gold (diamagnetic) and aluminum (paramagnetic). The thickness of each individual layer can range from tens to hundreds of nm. In at least one example each layer has a thickness of between 1 and 1000 nm.

Figure 3B:
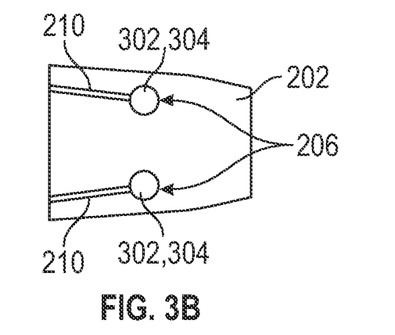

As shown in FIG. 3B, a buried signal line 210 can terminate at an exposed electrode 206. The electrode 206 exposed to the tissue in FIG. 3B can be of the diamagnetic material 302 or can be of the paramagnetic material 304. In at least one example, the electrode 206 can be fabricated of alternating layers of diamagnetic material 302 and paramagnetic material 304. The exposed electrode 206 can be configured for recording a physiological parameter.

Figure 3C:
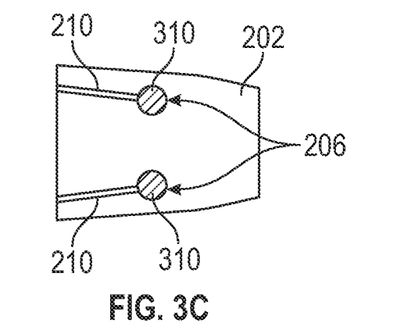

As shown in FIG. 3C the buried signal line 210 can terminate at an electrode 206, as described with reference to FIG. 3B that can further include a thin layer of carbon nanotubes (CNTs) 310 at the exposed electrode 206. The CNTs 310 increase the electrochemical surface area for interfacing with the neural tissue, thus increasing the signal-to-noise ratio (SNR). In one example, the thickness of the underlying alternating layers of diamagnetic 302 and paramagnetic 304 material is a total of 1 micron and the CNT 310 has a total thickness of 50 nm. In at least one example, the layer of CNT 310 can have a thickness of approximately 10-200 nm. In at least one example, the CNT layer 310 is relatively thin. In at least one example, the CNT layer 310 is thin because a carbon nanotube does not necessarily possess magnetic susceptibility close to that of neural tissue.

Figure 3D:
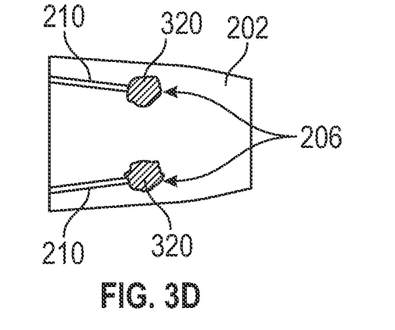

As shown in FIG. 3D, a layer of electrically conductive polymer 320 is deposited onto the exposed electrode 206 described with reference to FIG. 3B. The conductive polymer 320 has a rough surface and increases the electrochemical surface area, thus increasing the SNR. Because polymers generally have magnetic susceptibility close to neural tissue, the layer does not necessarily need to be very thin. An example of a conductive polymer 320 includes Poly(3,4-ethylenedioxythiophene), sometimes referred to as PEDOT.

Figure 3E:
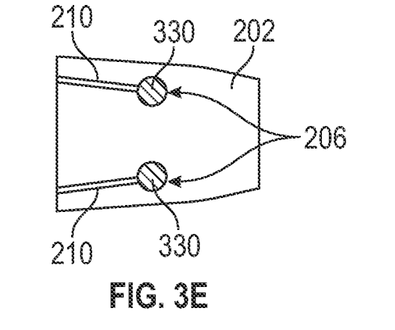

As shown in FIG. 3E, a thin layer of biocompatible conductive material 330 can be positioned over the exposed electrode 206 described with reference to FIG. 3B to improve the biocompatibility of the electrodes 206. Such a biocompatible conductive layer 330 may be advantageous depending on the composition of the underlying alternating layers of diamagnetic 302 and paramagnetic 304 material. The biocompatible conductive layer 330 can be fabricated by deposition, or by a removal process, or by a patterning technique (lithography). In at least one example, the biocompatible conductive material 330 can comprise gold (Au).

Figure 4A:
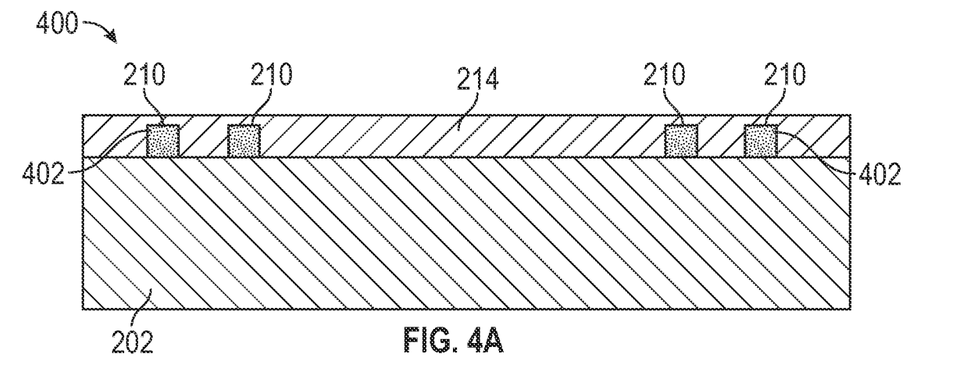
FIGS. 4A, 4B, 4C, 4D and 4E illustrate section and detail views of an electrode, in accordance with at least one embodiment.

FIG. 4A illustrates an example 400 of section view 222, and FIGS. 4B, 4C, 4D, and 4E illustrate examples of detail view 224. In the example 400, the signal lines 210 are fabricated of a metallic alloy 402 made by diffusion of diamagnetic and paramagnetic materials balanced in the correct volumetric ratio such that the effective bulk magnetic susceptibility is tunable to that of neural tissue. An example embodiment involves diffusion of gold (diamagnetic) and aluminum (paramagnetic). The alloy can be made by depositing very thin (for example, 5 nm or less than about 5 nm) alternating layers of diamagnetic and paramagnetic materials by evaporation followed by heating to promote diffusion. In one example, the diamagnetic and paramagnetic materials can be co-deposited by sputtering.

Figure 4B:
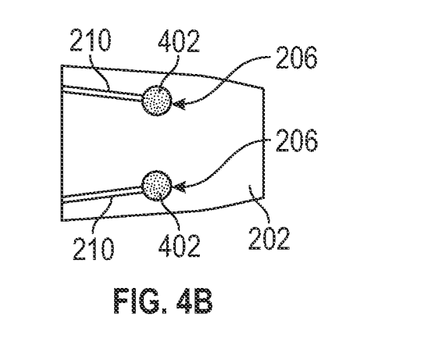

As shown in FIG. 4B, a buried signal line 210 can terminate at an exposed electrode 206. The electrode 206 exposed to the tissue can be a metallic alloy 402 made by diffusion of diamagnetic and paramagnetic materials.

Figure 4C:
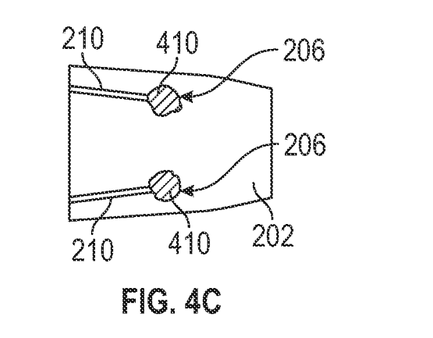

As shown in FIG. 4C the buried signal line 210 can terminate at an electrode 206, as described with reference to FIG. 4B, that can further include a thin layer of carbon nanotubes (CNTs) 410 at the exposed electrode 206. The CNTs 410 increase the electrochemical surface area for interfacing with the neural tissue, thus increasing the signal-to-noise ratio (SNR). In at least one example, the total thickness of the underlying alloy 402 can be about 1 micron or less. In at least one example, the total thickness of the underlying alloy 402 can be about 1 micron. In at least one example, the layer of CNT 410 can have a thickness of approximately 10-200 nm. In at least one example, the CNT 410 thickness can be about 50 nm or less. In at least one example, the CNT 410 thickness can be about 50 nm. In some embodiments, the CNT layer 410 is thin because CNTs do not necessarily possess magnetic susceptibility close to that of neural tissue.

Figure 4D:
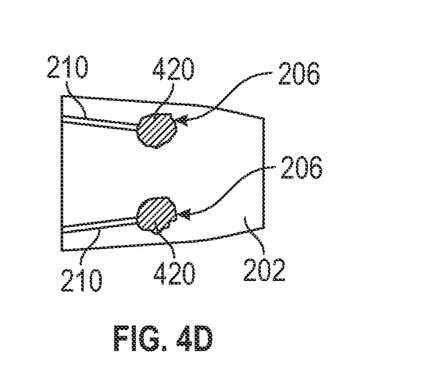

As shown in FIG. 4D, a layer of electrically conductive polymer 420 is deposited onto the exposed electrode 206 described with reference to FIG. 4B. The conductive polymer 420 has a rough surface and increases the electrochemical surface area, thus increasing the SNR. Because polymers generally have magnetic susceptibility close to neural tissue, the layer 420 does not necessarily need to be very thin. An example of a conductive polymer 420 includes Poly(3,4-ethylenedioxythiophene), sometimes referred to as PEDOT.

Figure 4E:
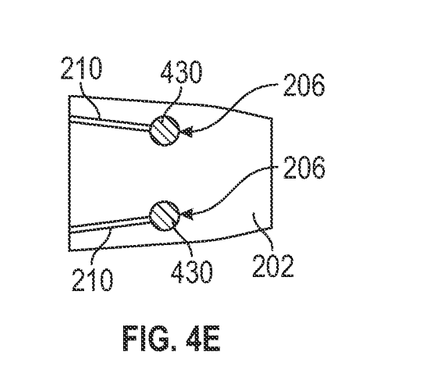

As shown in FIG. 4E, a thin layer of biocompatible conductive material 430 can be positioned over the exposed electrode 206 described with reference to FIG. 4B to improve the biocompatibility of the electrodes 206. Such a biocompatible conductive layer 430 may be advantageous depending on the composition of the underlying alloy. The biocompatible conductive layer 430 can be fabricated by deposition, or by a removal process, or by a patterning technique (lithography). In at least one example, the biocompatible conductive material 430 can comprise gold (Au).

Figure 5A:
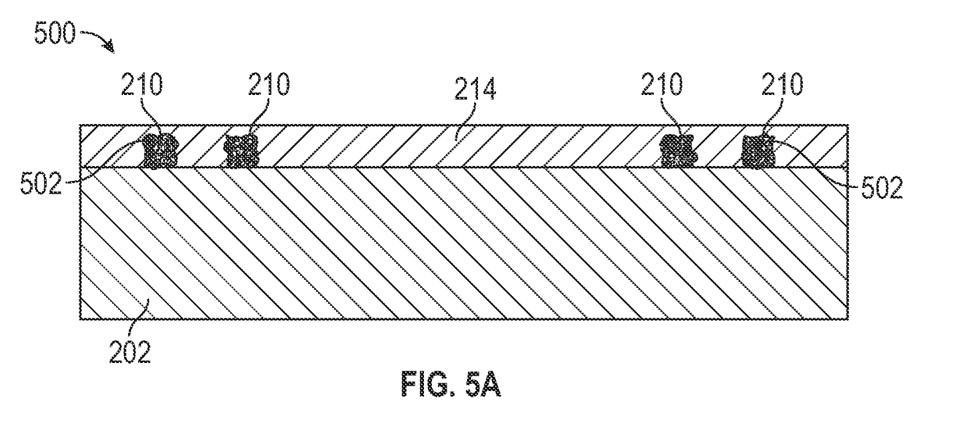
FIGS. 5A, 5B, 5C, 5D and 5E illustrate section and detail views of an electrode, in accordance with at least one embodiment.

FIG. 5A illustrates an example 500 of section view 222, and FIGS. 5B, 5C, 5D, and 5E illustrate examples of detail view 224. In the example 500 shown in FIG. 5A, the section view taken at 222-222 (with respect to FIG. 2) illustrates that the signal lines 210 are disposed on the substrate 202 and electrically isolated by the layer of insulation 214. In the illustrated example, the electrodes and signal lines 210 are fabricated of randomly oriented conductive nanorods 502 of diamagnetic and paramagnetic materials balanced in the correct volumetric ratio such that the effective bulk magnetic susceptibility is tunable to that of neural tissue. An example embodiment involves nanorods 502 of gold (diamagnetic) and aluminum (paramagnetic). The randomly oriented nanorods 502 can reduces the eddy currents caused by time-varying magnetic fields in MRI because induced currents will be in random directions and therefore opposing currents will cancel out. In addition, the randomly oriented nanorods 502 can increase surface roughness (and electrochemical surface area) at the exposed electrodes 206 to improve SNR. In at least one example, the randomly oriented conductive nanorods 502 can include a network of randomly oriented conductive materials selected from the group consisting of: conductive nanorods, nanomaterials, and micro-structured conductive materials.

Figure 5B:
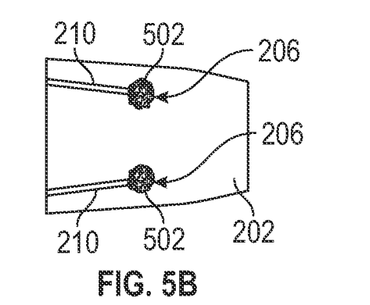

As shown in FIG. 5B, a buried signal line 210 can terminate at an exposed electrode 206. The electrode 206 exposed to the tissue in FIG. 5B can include randomly oriented conductive nanorods 502 of diamagnetic and paramagnetic materials.

Figure 5C:
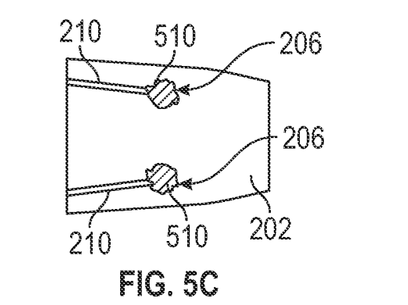
Figure 5D:
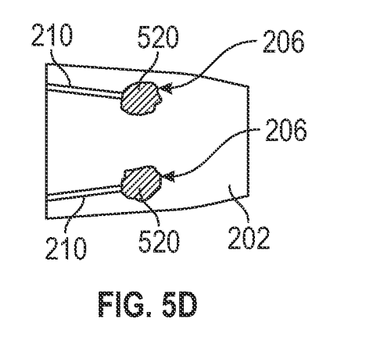

As shown in FIG. 5C the buried signal line 210 can terminate at an electrode 206, as described with reference to FIG. 5B, that can further include a thin layer of carbon nanotubes (CNTs) 510 at the exposed electrode 206. The CNTs 510 increase the electrochemical surface area for interfacing with the neural tissue, thus increasing the signal-to-noise ratio (SNR). In one example, the thickness of the underlying nanorod composite 502 can be about 1 micron or less and the CNT 510 can have a total thickness of about 50 nm or less. In at least one example, the thickness of the underlying nanorod composite 502 is about 1 micron. In at least one example, the layer of CNT 510 can have a thickness of approximately 10-200 nm. In at least one example, the CNT 510 has a thickness of about 50 nm. In at least one example, the CNT 510 is configured as a relatively thin layer. A carbon nanotube does not necessarily possess magnetic susceptibility close to that of neural tissue As shown in FIG. 5D, a layer of electrically conductive polymer 520 is deposited onto the exposed electrode 206 described with reference to FIG. 5B. The conductive polymer 520 has a rough surface and increases the electrochemical surface area, thus increasing the SNR. Because polymers generally have magnetic susceptibility close to neural tissue, the polymer layer 520 does not necessarily need to be very thin. An example of a conductive polymer 520 includes Poly(3,4-ethylenedioxythiophene), sometimes referred to as PEDOT.

Figure 5E:
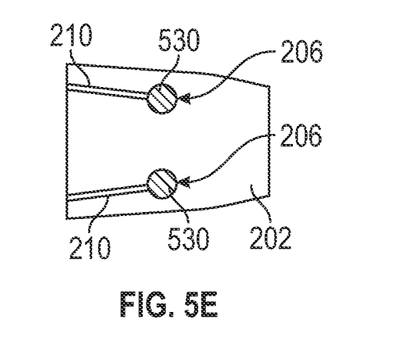

As shown in FIG. 5E, a thin layer of biocompatible conductive material 530 can be positioned over the exposed electrode 206 described with reference to FIG. 5B to improve the biocompatibility of the electrodes 206. Such a biocompatible conductive layer 530 may be advantageous depending on the composition of the randomly oriented conductive nanorods 502. The biocompatible layer 530 can be fabricated by deposition, or by a removal process, or by a patterning technique (lithography). In at least one example, the biocompatible conductive material 530 can comprise gold (Au).

Figure 6:
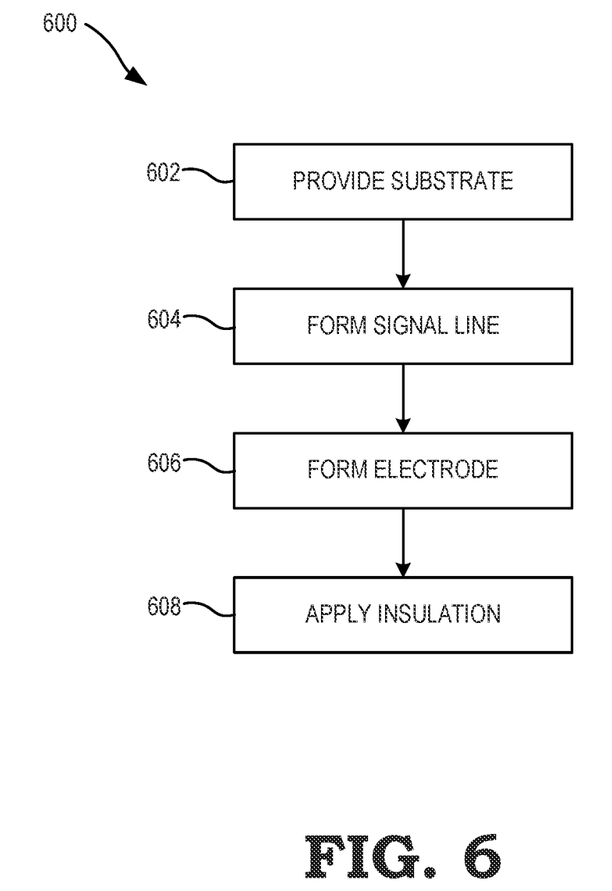
FIG. 6 is a flowchart illustrating an example method of fabricating an electrode, in accordance with at least one embodiment.

FIG. 6 is a flowchart illustrating an example method 600 of fabricating a neural recording/stimulating electrode, in accordance with at least one embodiment. At block 602, a substrate is provided. In at least one example, the substrate can be a polyimide substrate.

At block 604, at least one signal line is formed on the substrate. In at least one example, the at least one signal line can have a diamagnetic material and paramagnetic material in a ratio determined by the properties of physiological tissue. In at least one example, forming the signal line includes selecting a volumetric ratio between at least two materials. In at least one example, selecting the volumetric ratio includes selecting, based on a magnetic susceptibility of the signal line. In some examples, the volumetric ratio is selected to substantially match the magnetic susceptibility with that of the physiological tissue. In at least one example, the signal line is formed using gold. In at least one example, the signal line is formed using aluminum. In some examples, the signal line is formed using layers of diamagnetic material and paramagnetic material with respect to a physiological tissue. In some examples, the layers can have a thickness of between 1 and 1000 nm. In at least one example, the signal line is fabricated by diffusion. In at least one example, the signal line is formed by depositing layers. In some examples, the signal line is formed includes evaporating and heating. In some examples, forming the signal line includes co-depositing the diamagnetic material and the paramagnetic material. In at least one example, forming the signal line includes forming a network of randomly oriented conductive nanorods/nanomaterials. In some examples, forming the signal line includes using a common fabrication technique.

At block 606, at least one electrode is formed, and each electrode is coupled to a signal line generally in a one-to-one relationship. In some examples, the at least one electrode can have a diamagnetic material and paramagnetic material in a ratio determined by the properties of physiological tissue. In at least one example, block 606 further includes selecting the ratio to substantially match the magnetic susceptibility with that of the physiological tissue. In at least one example, forming the electrode includes selecting a volumetric ratio between at least two materials. In at least one example, the volumetric ratio is selected based on a magnetic susceptibility of the electrode. In some examples, the volumetric ratio is selected to substantially match the magnetic susceptibility with that of the physiological tissue. In at least one example, the electrode is formed using gold. In at least one example, the electrode is formed using aluminum. In some examples, the electrode is formed using layers of diamagnetic material and paramagnetic material with respect to a physiological tissue. In some examples, the layers can have a thickness of between 1 and 1000 nm. In at least one example, the electrode is fabricated by diffusion. In at least one example, the electrode is formed by depositing layers. In some examples, the electrode is formed includes evaporating and heating. In some examples, forming the electrode includes co-depositing the diamagnetic material and the paramagnetic material. In at least one example, forming the electrode includes forming a network of randomly oriented conductive nanorods/nanomaterials. In some examples, forming the electrode includes using a common fabrication technique.

In at least one example, the electrode is formed with a layer of carbon nanotubes at an exposed electrode surface. In some examples, the layer of carbon nanotubes can be formed to have a thickness of between approximately 10 and 200 nm. In some examples, the electrode can be formed with a layer of electrically conductive polymer at an exposed electrode surface, for example PEDOT. In at least one example, the electrode can be formed with a layer of biocompatible conductive material at an exposed electrode surface, for example gold. In at least one example, the electrodes are formed so as to provide a variety of MRI-compatible and biocompatible electrodes with particular susceptibility which matches the tissue susceptibility for neural recording and brain stimulation with minimal MRI susceptibility artifacts and tissue heating safety concern. In at least one example, the electrodes are applicable for other types of tissues and organs besides the brain. In some examples, the ratio of diamagnetic and paramagnetic material is determined by the properties of the physiological tissue. Generally, the properties of diamagnetic and paramagnetic are values relative to that of the tissue.

At block 608, insulation is selectively applied to the signal lines. In at least one example, the insulation is applied to electrically isolate the signal lines. In at least one example, the signal line is covered by the insulation layer.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

In at least one example, the term substantially means to a great or significant extent, nearly. In some examples, the term substantially may mean within plus or minus 10 percent.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A device comprising:
a substrate having a surface;
a signal line coupled to the substrate and covered by an insulation layer;
an electrical pad coupled to the signal line; and
an electrode coupled to the signal line, wherein at least one of the electrode and the signal line includes a plurality of conductors, the plurality of conductors including aluminum and including gold, wherein the plurality of conductors are configured based on a physiological susceptibility property of a tissue, wherein the plurality of conductors includes a plurality of nanorods and wherein the plurality of nanorods are randomly oriented.

2. The device of claim 1 wherein the plurality of conductors includes a plurality of layers.

3. The device of claim 2 wherein the plurality of layers includes a first layer of aluminum.

4. The device of claim 3 wherein the first layer is proximate the surface relative to a second layer of the plurality of layers.

5. The device of claim 3 wherein the plurality of layers includes a second layer of gold.

6. The device of claim 5 wherein the second layer is distal the surface relative to the first layer.

7. The device of claim 2 wherein the plurality of layers includes a first layer of gold.

8. The device of claim 1 wherein the plurality of conductors includes a polymer.

* * * * *